US00PP36171P2

(12) United States Plant Patent
Ioratti

(10) Patent No.: US PP36,171 P2
(45) Date of Patent: Oct. 1, 2024

(54) ***RUBUS* PLANT NAMED 'BT RASFIVE'**

(50) Latin Name: *Rubus idaeus*
Varietal Denomination: BT RASFIVE

(71) Applicant: Berrytech S.R.L., Baselga di Pine (IT)

(72) Inventor: Diego Ioratti, Baselga di Pine (IT)

(73) Assignee: Berrytech S.R.L. (IT)

( * ) Notice: Subject to any disclaimer, the term of this patent is extended or adjusted under 35 U.S.C. 154(b) by 0 days.

(21) Appl. No.: 18/540,195

(22) Filed: Dec. 14, 2023

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/0887
See application file for complete search history.

*Primary Examiner* — Kent L Bell

(57) ABSTRACT

A new and distinct cultivar of *Rubus* plant named 'BT RASFIVE' is disclosed, characterized by a very early primocane fruit period. Plants produce high to very high cane branching with a bushy semi-erect architecture and have a low chill requirement. Fruits are very firm and easy to store with a stable firmness after harvest. The new variety is a *Rubus*, normally produced as an outdoor garden or container plant.

2 Drawing Sheets

Latin name of the genus and species: *Rubus idaeus.*
Variety denomination: 'BT RASFIVE'.

BACKGROUND OF THE INVENTION

The new *Rubus* cultivar is a product of a planned breeding program conducted by the inventor in Borgo Valsugana, Italy. The objective of the breeding program was to produce new *Rubus idaeus*varieties for commercial applications. The cross resulting in this new variety was made during September of 2019.

The seed parent is the, unpatented proprietary variety referred to as *Rubus* 'BP17CF338'. The pollen parent is the unpatented variety *Rubus* 'BTNH'. The new variety was selected during September of 2020 by the inventor in a group of seedlings resulting from the 2019 crossing, in a research greenhouse in Borgo Valsugana, Italy.

Asexual reproduction of the new cultivar was performed by vegetative suckers. This was first performed at a research greenhouse in Baselgia di Pine, Italy between December of 2020 and February of 2021 and has shown that the unique features of this cultivar are stable and reproduced true to type in multiple successive generations.

SUMMARY OF THE INVENTION

The cultivar 'BT RASFIVE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BT RASFIVE'. These characteristics in combination distinguish 'BT RASFIVE' as a new and distinct *Rubus* cultivar:

1. Very early primocane fruiting period.
2. Branching of the cane is high to very high.

3. The plant has a very low chill requirement, often not necessary with a green cutback during late summer which allow the unproductive buds to budbreak and get into fruiting without application of chill.
4. Bushy semierect architecture of the plant.
5. Fruits are very firm and easy to store with a stable firmness post-harvest.

PARENT COMPARISON

Plants of the new cultivar 'BT RASFIVE' are similar to plants of the seed parent, in most horticultural characteristics, however, plants of the new cultivar 'BT RASFIVE' differ in the following:

1. The new variety is more productive both on primocane and on floricane harvest.
2. The new variety is less spiny than the seed parent.
3. The new variety produces more branches.
4. The new variety produces larger fruits.
5. Color of the fruit is more consistent compared to fruit of the seed parent.

Plants of the new cultivar 'BT RASFIVE' are similar to plants of the pollen parent, in most horticultural characteristics, however, plants of the new cultivar 'BT RASFIVE' differ in the following:

1. The new variety has a clearer(less muddled) fruit color than the pollen parent.
2. The new variety is less spiny than the pollen parent.
3. The new variety is more productive on primocane fruiting than the pollen parent.
4. The new variety produces more shoots for plant renewal.
5. Color of the fruit is more consistent compared to fruit of the pollen parent.

COMMERCIAL COMPARISON

Plants of the new cultivar 'BT RASFIVE' are comparable to the variety *Rubus* 'BT RASTWO', U.S. Plant Pat. No.

33,447. The two *Rubus* varieties are similar in most horticultural characteristics, however, the new variety 'BT RASFIVE' differs in the following:

1. The new variety is more productive both on primocane and on floricane harvest.
2. The new variety has a more stable color in postharvest with dryer fruit pulp.
3. The new variety is less spiny, both in density of the thorns and sharpness.
4. The new variety is earlier (about 20 days) in primocane fruiting.
5. The new variety has a more erect architecture.

Plants of the new cultivar 'BT RASFIVE' can also be compared to the commercial variety *Rubus* 'BP1' U.S. Plant Pat. No. 22,459). These varieties are similar in most horticultural characteristics however, the new variety 'BT RASFIVE' differs in the following:

1. The new variety is more productive both on primocane and on floricane harvest.
2. The new variety has a more stable color in postharvest with dryer fruit pulp.
3. The new variety has a more erect architecture.
4. The new variety is less spiny, both in density of the thorns and sharpness.
5. The new variety is earlier in production (about 5 days) in primocane fruiting.

BRIEF DESCRIPTION OF THE PHOTOGRAPHS

The photographs were taken using conventional techniques and although colors may appear different from actual colors due to light reflectance it is as accurate as possible by conventional photographic techniques. Colors in the photographs may appear to differ slightly from the color values cited in the botanical description, which accurately describe the colors.

DETAILED BOTANICAL DESCRIPTION

Figure 1:
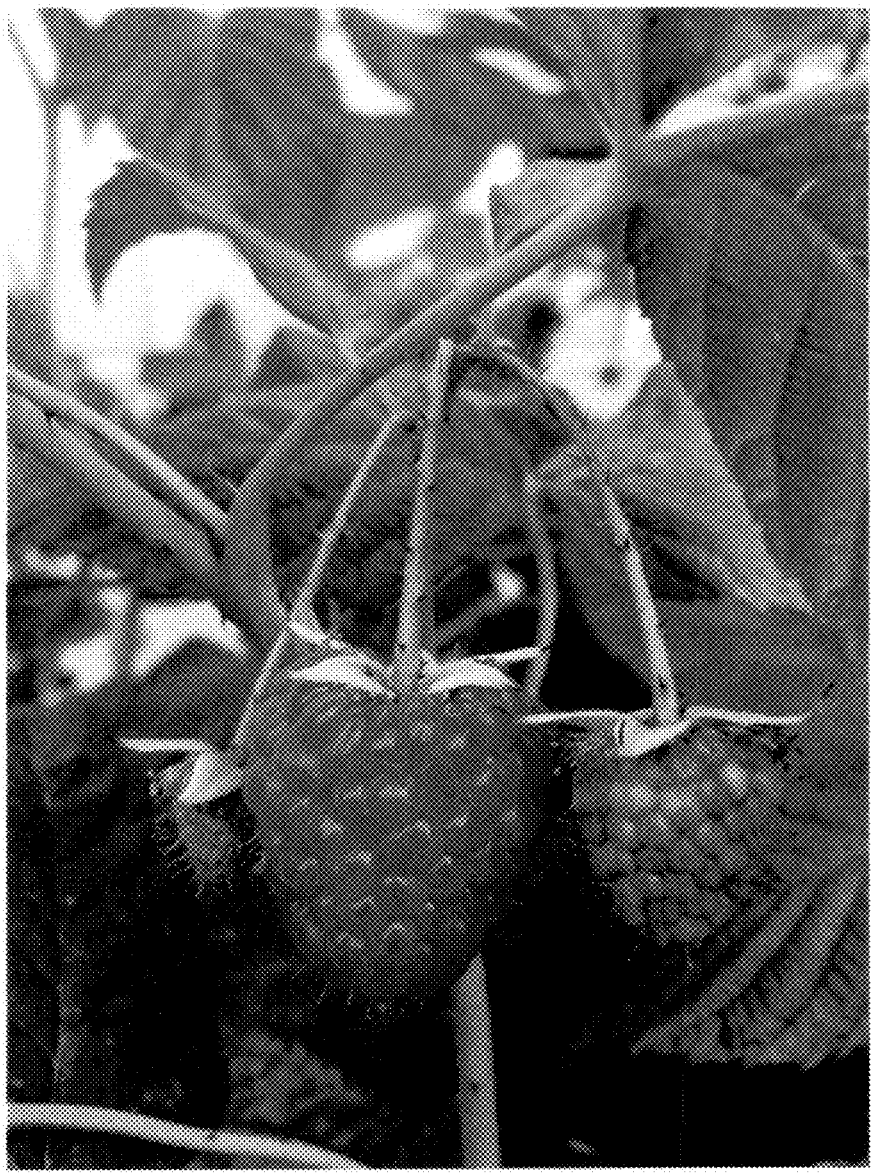
FIG. 1 illustrates in full color a typical ripe and unripe fruit still on the plant of the new variety.
Figure 2:
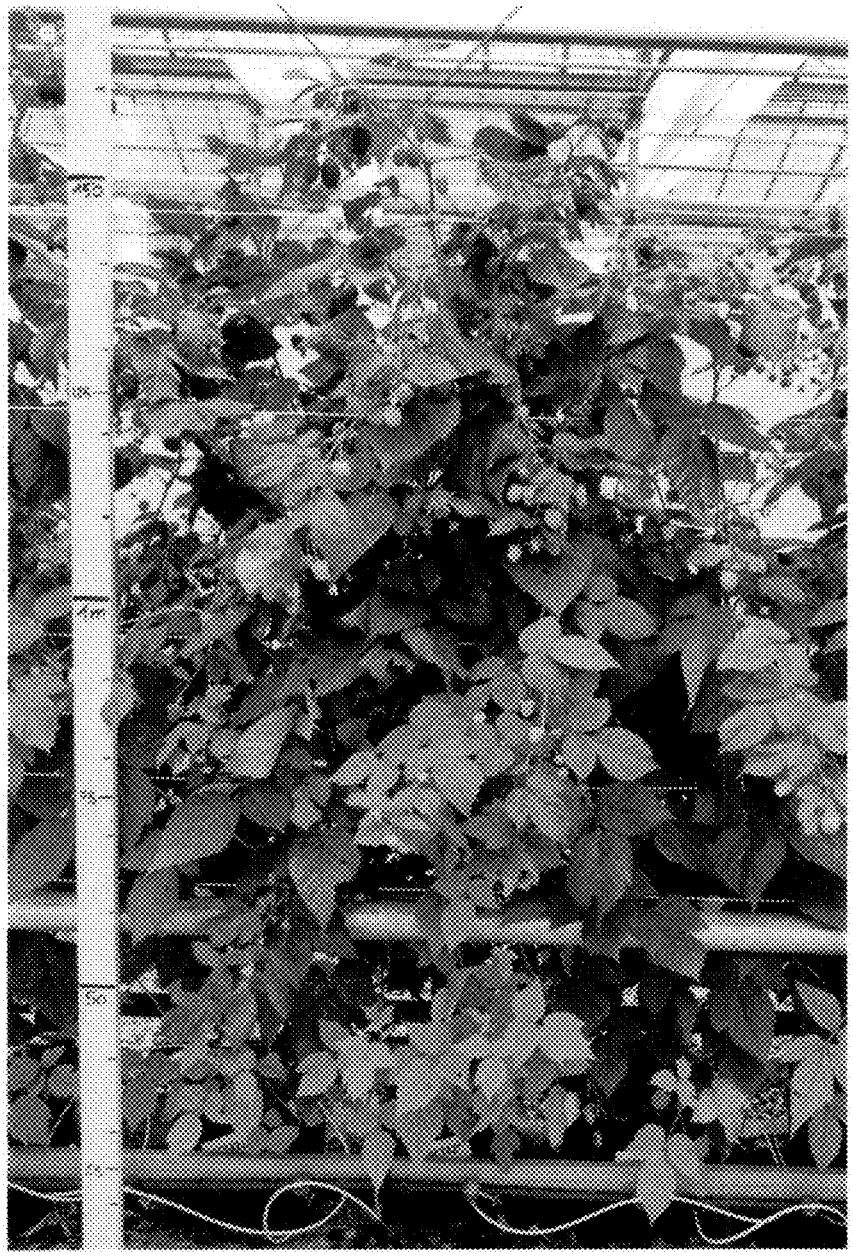
FIG. 2 illustrates in full color a typical fruiting plant of 'BT RASFIVE'. Age of the plant is approximately 1 year, grown in a poly hoop house.

In the following description, color references are made to The Royal Horticultural Society Colour Chart 2007 except where general terms of ordinary dictionary significance are used. The following observations and measurements describe 'BT RASFIVE' plants which were grown in Levico Terme, Trento, Italy. Plants were grown in a season tunnel, given approximately 30% shading during Summer. The growing temperature ranged from about 15° C. to 34° C. during the day and from about 8° C. to 22° C. during the night. Measurements and numerical values represent averages of typical plant types. Plants are approximately 1 year old.

Botanical classification: *Rubus idaeus* 'BT RASFIVE'.

PROPAGATION

Time to initiate roots: About 35 days at approximately 16° C.

Time to produce a rooted cutting: About 45 days at 18 ° C.

PLANT

Age of plant described: About 1 year.

Plant spread: Approximately 90 cm.

Plant height: Approximately 150 cm.

Habit: Semi-upright.

Primocane length: Approx. 160 cm.

Primocane color: Near RHS Yellow-Green N150B.

Anthocyanin coloration present: Not typical.

Dormant cane color: Near RHS Grey-Brown 199C.

Primocane diameter: Average 1 cm.

Internode length: Average 5 cm.

Spines:

*Approximately density/quantity of spines.*—Approximately 3 per 4 per cm of stem length at 1 meter of height.

*Length.*—Average range 2 to 3 mm.

*Color.*—Near RHS Brown N200B.

*Shape.*—Deltate.

FOLIAGE

Leaf:

*Arrangement.*—Compound opposite.

*Quantity.*—9-10 per stem.

*Average length.*—Approximately 17 to 18 cm.

*Average width.*—Approximately 16 to 17 cm.

Leaflet:

*Quantity.*—Most common quantity of leaflets per leaf: 3.

*Average length.*—Approximately 13-17 cm.

*Average width.*—Approximately 8-11 cm.

*Shape of blade.*—Overall broad deltate to ovate.

*Apex.*—Acuminate.

*Base.*—Broad rounded.

*Margin.*—Double serrate.

*Texture of top surface.*—Coriaceous.

*Texture of bottom surface.*—Coriaceous.

*Pubescence.*—Very little.

*Leaf internode length.*—5-7 cm.

*Color.*—Young foliage upper side: Near RHS Yellow-Green 144B. Young foliage under side: Near RHS Green 142C. Mature foliage upper side: Near RHS Green 143A. Mature foliage under side: Near RHS Green 134B.

*Venation.*—Type: Cross veniculate, pinnate along main axis. Venation color upper side: Near Yellow-Green 144C. Venation color under side: Near Yellow-Green 144D.

*Petiole.*—Length: 7 cm. Width: 3 mm. Color: Near RHS Yellow-Green N144C. Texture: Glabrous.

*Rachis.*—Length: 12-13 cm. Width: 3-4 mm. Color: Near RHS Yellow-Green N144C. Texture: Glabrous.

*Stipules.*—Not observed.

FLOWER

Floral bud burst date: Approximately July 1 for primocane flowers.

Flowering season: Begins around July 15 in Verona, Italy.

Inflorescence:

*Flowers per.*—15-24.

Flower size:

*Diameter.*—Approximately 2 cm.

*Length.*—Approximately 1 cm.

Peduncle:

*Length.*—5 cm.

*Diameter.*—2 mm.

*Color.*—Near RHS Yellow-Green N144B.

*Texture.*—Glabrous.

Pedicel:
*Length.*—1.3 cm.
*Diameter.*—2 mm.
*Color.*—Near RHS Yellow-Green N144B.
*Texture.*—Glabrous.

Petals:
*Petal arrangement.*—Rotate.
*Length.*—9 mm.
*Width.*—5 mm.
*Shape.*—Semi-cuneate.
*Margin.*—Entire.
*Apex.*—Rounded.
*Base.*—Rounded.
*Petal quantity.*—5.
*Texture.*—Glabrous.

Color:
*Petals.*—When opening: Upper surface: Near RHS White N155B. Lower surface: Near RHS White N155B. Fully opened: Upper surface: Near RHS White N155B. Lower surface: Near RHS White N155B.

Bud:
*Shape.*—Ovate.
*Length.*—Approximately 6 mm.
*Diameter.*—Approximately 4 mm.
*Color.*—Near RHS Yellow-Green 144B.

Sepals:
*Length.*—1.5 cm.
*Width.*—6 mm.
*Shape.*—Narrow deltate with apiculate apex.
*Color.*—Interior Surface: Near RHS Green 140C. Exterior Surface: Near RHS Green 141B.
*Texture.*—Glabrous.

REPRODUCTIVE ORGANS

Androecium:

Stamens:
*Number.*—120.
*Filament length.*—Approximately 6 mm.
*Filament color.*—Near RHS Green-White 157A.

Anthers:
*Length.*—0.8 mm.
*Shape.*—Ovate.
*Color.*—Near RHS Greyed-Orange 164A.
*Pollen.*—Quantity: Abundant. Color: Near RHS White N155C.

Pistil:
*Number.*—120 to 130.
*Length.*—Approximately 4.5 mm.
*Style.*—Length: Approximately 4 mm. Color: Near RHS Green-White 157A.

FRUIT

Market use: Fresh consumption.
Length: 4 cm.
Diameter: 3 cm.
General shape in lateral view: Conical-round.
Color: Near RHS Red 45B, 45C and 45D, darkest coloration near fruit distal end.
Average drupelets per berry: 150.
Average weight per berry: 5.5 grams
Fruit bearing on floricane/primocane or both: Both
Fruit begins ripening: Primocane about July 20; floricane about April $15^{th}$.
Fruiting season: Primocane about mid-July to mid-October; floricane end of May to end of June.
Yield per hectare: 20 to 25 ton/ha in primocane; 15 to 18 ton/ha in floricane
Other fruit characteristics: Very stable color and firmness post-harvest. Shelf life of about one week at 4° C. without loss of quality.

OTHER CHARACTERISTICS

Disease/pest resistance: Observed good tolerance for raspberry aphid, *Amphorophora idaei* and leafhoppers, *Edwardsiana rosae*. No observed resistance nor susceptibility to normal diseases of *Rubus*.
Temperature tolerance: Maximum 36° C. during pollination and harvest.

What is claimed is:

1. A new and distinct cultivar of *Rubus* plant named 'BT RASFIVE' as herein illustrated and described.

* * * * *